United States Patent

Théron

[11] Patent Number: 6,156,005
[45] Date of Patent: *Dec. 5, 2000

[54] BALLON CATHETER FOR STENT IMPLANTATION

[75] Inventor: Jacques Théron, Fleury sur Orne, France

[73] Assignee: Schneider (Europe) GmbH, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/991,848

[22] Filed: Dec. 16, 1997

[30] Foreign Application Priority Data

Oct. 23, 1997 [EP] European Pat. Off. ............ 97203280

[51] Int. Cl.$^7$ .................................................. A61M 29/00
[52] U.S. Cl. ............................... 604/96; 604/101; 604/99
[58] Field of Search ................... 604/96, 97, 101, 604/93, 99, 915, 917, 919, 920, 921; 606/194, 195, 198, 108

[56] References Cited

U.S. PATENT DOCUMENTS

| | | | |
|---|---|---|---|
| 3,173,418 | 3/1965 | Baran | 604/920 |
| 3,982,544 | 9/1976 | Dyck | 128/349 R |
| 4,333,452 | 6/1982 | Au | 128/205.24 |
| 4,655,746 | 4/1987 | Daniels et al. | 604/53 |
| 4,697,574 | 10/1987 | Karcher et al. | 604/118 |
| 4,733,665 | 3/1988 | Palmaz | 606/108 |
| 4,771,777 | 9/1988 | Horzewski et al. | 128/344 |
| 5,152,277 | 10/1992 | Honda et al. | 604/101 |
| 5,158,553 | 10/1992 | Berry et al. | 604/248 |
| 5,334,153 | 8/1994 | McIntyre et al. | 604/99 |
| 5,397,307 | 3/1995 | Goodin | 604/96 |
| 5,403,274 | 4/1995 | Cannon | 604/9 |
| 5,423,742 | 6/1995 | Théron | 604/28 |
| 5,462,529 | 10/1995 | Simpson et al. | 604/101 |
| 5,599,307 | 2/1997 | Bacher et al. | 604/101 |
| 5,603,721 | 2/1997 | Lau et al. | 606/195 |
| 5,607,466 | 3/1997 | Imbert et al. | 623/1 |
| 5,632,760 | 5/1997 | Sheiban et al. | 606/191 |
| 5,645,529 | 7/1997 | Fagan et al. | 604/101 |
| 5,695,498 | 12/1997 | Tower | 606/108 |
| 5,709,701 | 1/1998 | Parodi | 606/194 |
| 5,728,068 | 3/1998 | Leone et al. | 604/101 |
| 5,782,909 | 7/1998 | Quiachon et al. | 623/1 |
| 5,807,330 | 9/1998 | Teitelbaum | 604/96 |

FOREIGN PATENT DOCUMENTS

| | | |
|---|---|---|
| 0277367A1 | 8/1988 | European Pat. Off. . |
| 0650740A1 | 5/1995 | European Pat. Off. . |
| 0747088A1 | 12/1996 | European Pat. Off. . |
| 0775470A1 | 5/1997 | European Pat. Off. . |
| WO 97/44082 | 11/1997 | WIPO . |
| WO 97/44085 | 11/1997 | WIPO . |
| WO 98/38930 | 9/1998 | WIPO . |

*Primary Examiner*—Sharon Kennedy
*Attorney, Agent, or Firm*—Crompton, Seager & Tufte, LLC

[57] ABSTRACT

A catheter device for the treatment of a vessel carrying body fluid, comprising an inner first occlusion catheter, having a first tubular shaft with a proximal end and a distal end, a distal occlusion balloon disposed at the distal end of the first tubular shaft and an inflation lumen extending through the first tubular shaft between a proximal entry at the proximal end and a distal exit inside the distal occlusion balloon, and an outer treatment catheter, having a second tubular shaft with a central lumen extending therethrough for coaxial reception of the first occlusion catheter, and being longitudinally displaceable with respect to the first occlusion catheter, further comprises a seal for the proximal entry of the inflation lumen, having an outside dimension small enough to fit within the central lumen for advancing, resp. withdrawing, a treatment catheter proximally onto, resp. from, the sealed first occlusion catheter, treatment catheters are exchangeable while the distal occlusion balloon is maintained in its inflated condition.

11 Claims, 3 Drawing Sheets

BALLON CATHETER FOR STENT IMPLANTATION

BACKGROUND OF THE INVENTION

This application claims priority under 35 U.S.C. § 119 of European Patent Application No. 97203280.9, filed in the European Patent Office on Oct. 23, 1997.

The invention relates to a catheter device for the treatment of a vessel carrying body fluid, comprising an inner first occlusion catheter, having a first tubular shaft with a proximal end and a distal end, a distal occlusion balloon disposed at the distal end of the first tubular shaft and an inflation lumen extending through the first tubular shaft between a proximal entry at the proximal end and a distal exit inside the distal occlusion balloon, and an outer treatment catheter, having a second tubular shaft with a central lumen extending therethrough for coaxial reception of the first occlusion catheter, and being longitudinally displaceable with respect to the first occlusion catheter.

A catheter device of the kind mentioned in the introduction is known for example from U.S. Pat. No. 5,423,742 which is used for percutaneous transluminal angioplasty of arteriosclerotic deposits or atheroma in the carotid artery. For this treatment an outermost guide catheter is pushed through an opening in the inguinal region of the patient into the vessel, until its front opening is situated directly in front of the stenosis. An innermost occlusion catheter is then inserted into the guide catheter and placed in a way that the occlusion balloon can be stabilized in the inflated state distal of the stenosis. A central dilation catheter is then pushed over the occlusion catheter, and the dilatation balloon is positioned in the middle of the stenosis which is now dilated in a known manner. Vessel parts which might be detached during angioplasty are prevented by the occlusion balloon from getting into the narrow and tortuous cerebral vessel system reducing thereby the risk of embolism.

After treatment of the stenosis the dilatation balloon is emptied and the dilation catheter is retracted. With the occlusion catheter simultaneously inflated, vessel fluid and any detached particles present are removed by suction through the guide catheter by means of a syringe. As a result of pressure exerted by means of the syringe, vessel fluid with small particles can be washed out reaching areas of the vessel where there is no danger of embolism. Finally, the occlusion balloon is also returned to the emptied state and the catheter device is removed from the vessel.

For inflating and deflating the occlusion balloon a syringe is connected to the proximal end of the occlusion catheter. The latter must have a length greater than the length of the guide catheter plus the length of the dilation catheter, for example between 250 and 300 cm, to allow the dilation catheter being withdrawn over the occlusion catheter completely out of the guide catheter, while the occlusion balloon remains in its inflated condition. The syringe connector which might be a stop cock combines the occlusion catheter and the dilation catheter to a unit which shows disadvantages if further treatment, such as stenting or post-dilating of the widened stenosis, is necessary. The catheter unit does not allow the exchange of the dilation catheter by another catheter during the protective occlusion balloon is kept in its inflated condition, since the connector forms an obstacle which cannot be passed through the central lumen of the dilation catheter. Thus, in such a case the whole catheter unit must be replaced. On one hand this might be a rather time consuming procedure putting a lot of stress to the patient. On the other hand it raises the risk of embolism since the protective downstream occlusion of the vessel has to be interrupted.

All documents cited herein, including the foregoing, are incorporated herein by reference in their entireties for all purposes.

SUMMARY OF THE INVENTION

It is therefor an object of the invention to provide a catheter device as described above which allows the exchange of a treatment catheter by another one while the occlusion catheter remains in place maintaining the occlusions ballon in its inflated condition for sealing the vessel distal of the portion to be treated.

Where the catheter device comprises a seal for the proximal entry of the inflation lumen, having an outside dimension small enough to fit within the central lumen for advancing, resp. withdrawing, a treatment catheter proximally onto, resp. from, the sealed first occlusion catheter, it is possible to exchange treatment catheters over the positioned occlusion catheter. During replacement the seal keeps maintaining the occlusion balloon in its inflated state and does not form a stopping obstacle.

In a preferred embodiment of the invention the treatment catheter is a dilatation catheter further having a non-compliant dilatation balloon whereby subsequent treatment of a stenosis with dilatation balloons of different diameters or lengths is possible. Such ballon dilatation catheters are well known in the art, see for example EP 0 650 740 A1, and have to be adapted in their central lumen which is usually sized for the reception of a guidewire. Thus, known balloon catheter technology can be used with a slight change in a lumen diameter. In a further embodiment of the invention a balloon-expandable stent is mounted on the dilatation balloon taking advantage of the fact that dilatation catheter are commonly used instruments for the deployment of balloon-expandable stents, it is referred to U.S. Pat. No. 4,733,665 as an example. Accordingly, such a treatment catheter allows scaffolding of a predilated stenosis by implanting a balloon-expandable stent immediately after having widened the stricture and while the downstream vessel system is still protected by the filled occlusion balloon.

In another preferred embodiment of the invention the treatment catheter is a stent delivery instrument loaded with a self-expanding stent. Self-expanding stents are also well known in the art and are special in that they comprise an unconstrained large diameter state which is taken by self-expansion upon removing the constraint which keeps the tubular stent in a compressed small diameter condition. For insertion into the vessel system such a stent can be loaded distally into the lumen of an outer shaft of a delivery instrument, such as it is disclosed in EP 0 775 470 A1. Having reached the treatment site the outer shaft is withdrawn relative to an inner shaft which works as a plunger keeping the axial position of the stent while the constraint applied by the outer shaft is removed from the stent to release it. Delivery instruments for self-expanding stents are also usually inserted over a guide wire which is passed through a central lumen of the instrument. By adaption of the central guide wire lumen the deployment of self-expanding stents following balloon angioplasty is possible.

In a further preferred embodiment of the invention the treatment catheter is a second occlusion catheter further having a proximal occlusion balloon for sealing a vessel portion between the proximal and distal occlusion balloon. Due to the fact that the occlusion catheters are displaceable with respect to each other the length of the vessel portion to be sealed is adjustable. U.S. Pat. No. 4,655,746 is incorporated herewith as a reference. The sealing can provide for a well visible access to this protion in a surgical intervention. Moreover, if according to a further preferred embodiment an annular lumen is disposed between the first and second occlusion catheter and extends between a proximal inlet and a distal outlet for infusion, resp. aspiration, of a liquid into, resp. from, the sealed vessel portion, drugs can be delivered locally to a vessel portion, i.e., without affecting the rest of the vessel system, and any reaction products or particles can be aspirated through said annular lumen.

In a further preferred embodiment of the invention the catheter device futher comprises an outer insertion catheter having a third tubular shaft with a through lumen for insertion, resp. retraction, of the first occlusion catheter and of a treatment catheter into, resp. from, the vessel to be treated. This catheter serves as a guide for the occlusion and treatment catheters finding their way from the puncture which is usually placed in the inguinal region through the vessel system having a larger diameter to the portion to be treated. It is kept in place during all manipulations and can finally be used to rinse off small particles detached from the vessel wall during the treatment before the protective distal occlusion is removed.

In sum, the present invention relates to a catheter device for the treatment of a vessel carrying body fluid. The catheter has an inner first occlusion catheter, having a first tubular shaft with a proximal end and a distal end, a distal occlusion balloon disposed at the distal end of the first tubular shaft and an inflation lumen extending through the first tubular shaft between a proximal entry at the proximal end and a distal exit inside the distal occlusion balloon, and an outer treatment catheter, having a second tubular shaft with a central lumen extending therethrough for coaxial reception of the first occlusion catheter, and being longitudinally displaceable with respect to the first occlusion catheter. The device has a seal for the proximal entry of the inflation lumen, having an outside dimension small enough to fit within the central lumen for advancing, resp. withdrawing, a treatment catheter proximally onto, resp. from, the sealed first occlusion catheter. The catheter may be a dilatation catheter further having a non-compliant dilatation balloon and a balloon-expandable stent mounted on the dilatation balloon. The catheter may be a stent delivery instrument loaded with a self-expanding stent. The catheter may be a second occlusion catheter further having a proximal occlusion balloon, for sealing a vessel portion between the proximal and distal occlusion balloon, optionally with an annular lumen disposed between the first and second occlusion catheter and extending between a proximal inlet and a distal outlet for the infusion, resp. aspiration, of a liquid into, resp. from, the sealed vessel portion. The catheter device may further have an outer insertion catheter having a third tubular shaft with a through lumen for insertion, resp. retraction, of the first occlusion catheter and of a treatment catheter into, resp. from, the vessel.

BRIEF DESCRIPTION OF THE DRAWINGS

Further advantages are readily apparent from an exemplary embodiment of the invention described with reference to the drawings in which.

DETAILED DESCRIPTION OF THE INVENTION

Figure 1:
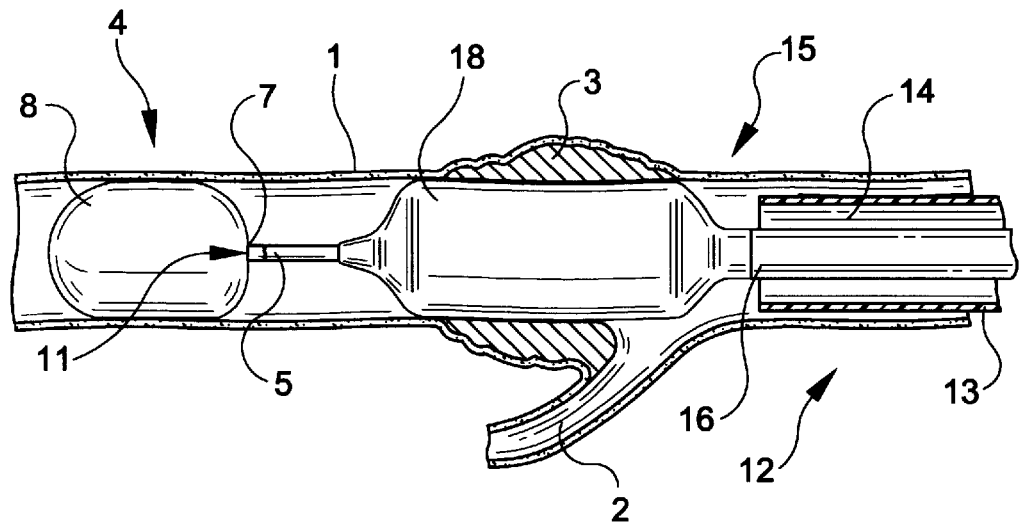
FIGS. 1 and 4–6 show schematic representations of a vessel section with an inserted catheter device according to the invention.

FIGS. 1 and 4–6 show a portion . of a blood vessel 1 which, downstream from a lateral branch 2, was partially closed by a stenosis formed by arterial plaque deposit 3. The inserted catheter device comprises an inner first occlusion catheter 4 having a first tubular shaft 5 with a proximal end 6 (not shown) and a distal end 7, a distal occlusion balloon 8 and an inflation lumen 9 extending through the first tubular shaft 5 between a proximal entry 10 (not shown) and a distal exit 11 inside the distal occlusion balloon 8. The distal occlusion balloon 8 is disposed at the distal end 7 of the first tubular shaft 5 and is positioned in its inflated condition distally of the area affected by plaque deposit 3. This is to establish a protective seal for particles detached from the vessel wall during the treatment. The first occlusion catheter 4 and treatment catheters 5, 22, 15' are inserted and retracted through an insertion catheter 12 having a third tubular shaft 13 with a through lumen 14.

According to FIG. 1 the plaque deposit 3 is forced into the wall of the vessel portion 1 by known balloon dilatation technique performed with a dilatation catheter 15 having a second tubular shaft 6 with a central lumen 17 (not shown) extending therethrough for coaxial reception of the first occlusion catheter 4 and being longitudinally displaceable with respect to the first occlusion catheter 4. After dilation the dilatation balloon 18 is emptied and withdrawn through the insertion catheter 12 over the first occlusion catheter 4.

Figure 2:
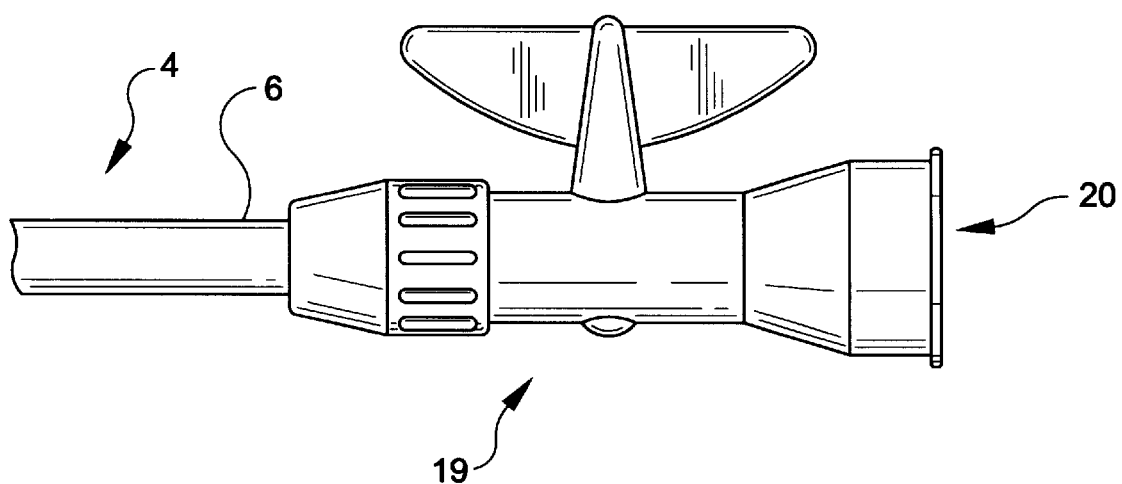
FIG. 2 shows the proximal end of the first occlusion catheter according to the invention connected to a stop cock.

FIG. 2 shows the proximal end 6 of the first occlusion catheter 4 which is connected to a stop cock 19. Before balloon dilatation the distal occlusion balloon 8 was filled with an inflation medium such as physiological saline or fluoroscopic contrast which is set under pressure for example by a syringe (not shown) placed into the proximal opening 20 of the stop cock 19. The pressurized condition is maintained during the treatment procedure by switching the stop cock 19 into its locking position. After balloon dilatation the dilatation catheter 15 can only be withdrawn until it reaches the stop cock 19 as it was in the prior art situation.

Figure 3:
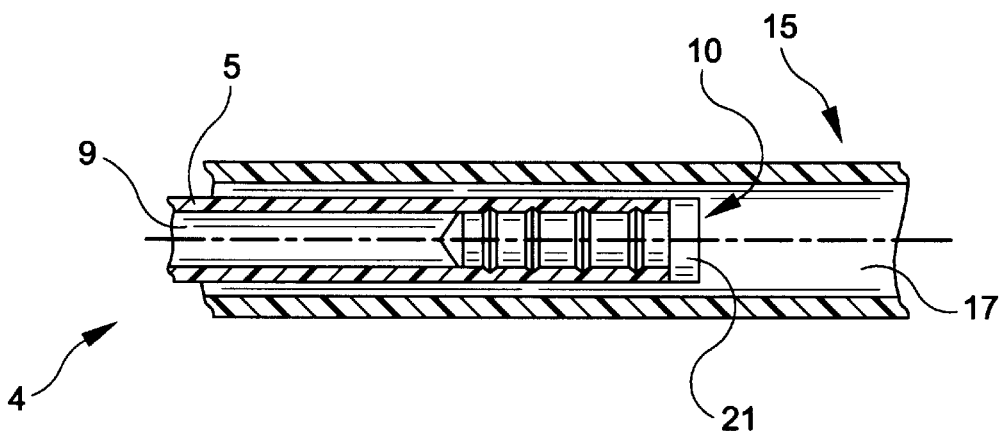
FIG. 3 shows a longitudinal section through the sealed proximal end of the catheter device.

In order to remove the dilatation catheter 15 completely from the first occlusion catheter 4 the inflation lumen 9 is occluded by clamping or kinking the first tubular shaft 5 distal of the stop cock 19. In this state the stop cock 19 is replaced by a seal 21 which is plugged into the proximal entry 10 of the inflation lumen 9. According to FIG. 3 the seal 21 has an outside dimension small enough to fit within the central lumen 17 of the dilatation catheter 15 which therefor can be withdrawn proximally from the sealed first occlusion catheter 4. The occlusion catheter 4 still fulfills its function of occluding the vessel 1 downstream of the treatment portion and is ready to receive another treatment catheter if indicated.

Figure 4:
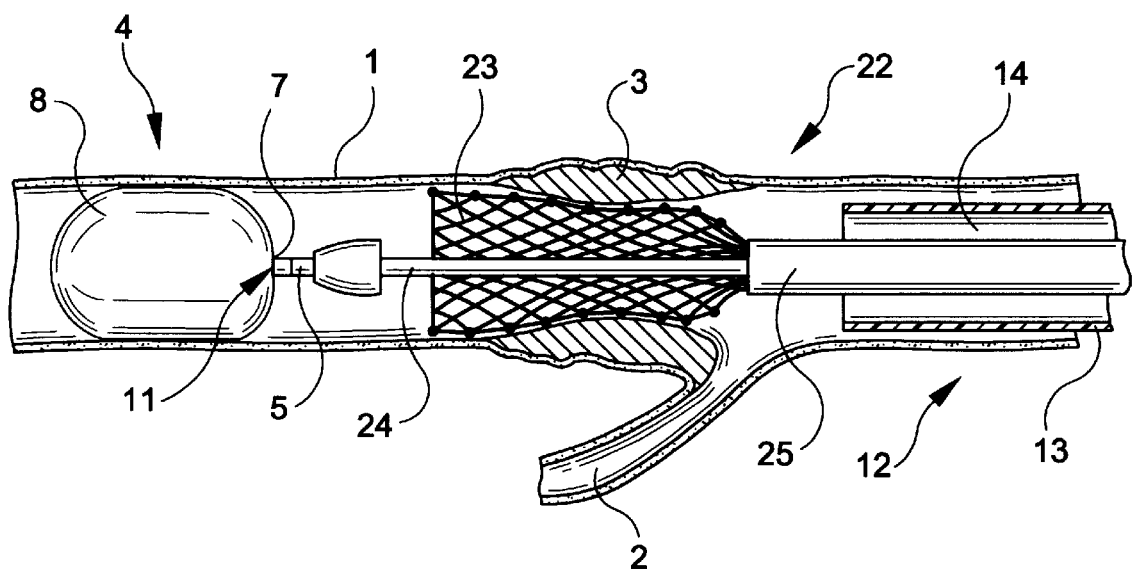
Figure 5:
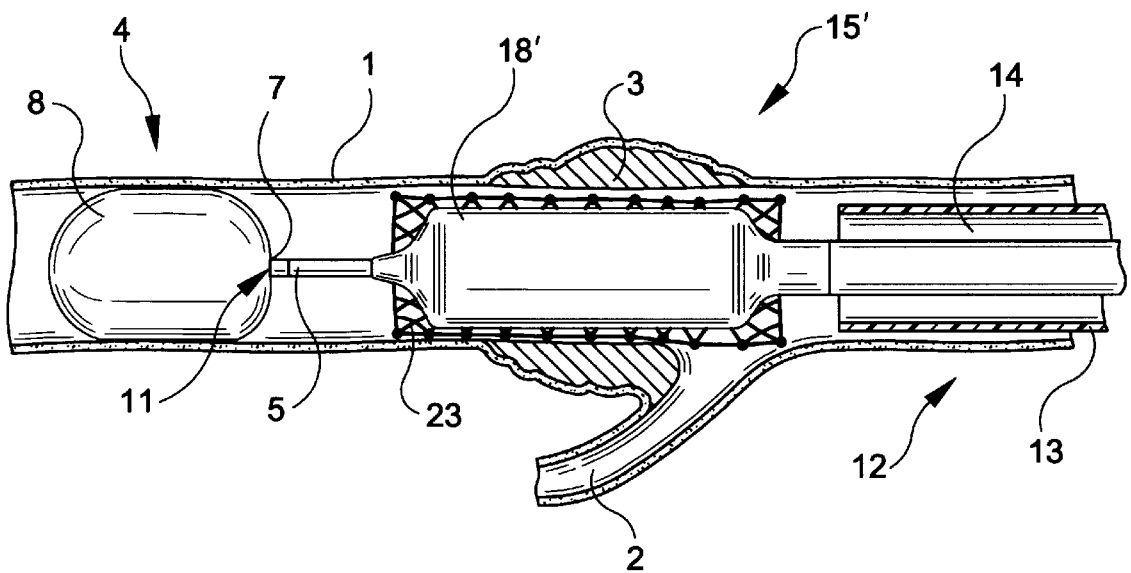

In case the widened stenosis requires stenting, i.e. scaffolding the treated vessel portion 1 by implanting a vessel supporting tubular member to prevent restenosis, a stent delivery instrument 22, as shown in FIG. 4, loaded with a self-expanding stent 23 is introduced over the first occlusion catheter 4. For insertion the self-expanding stent 23 is radially compressed and kept in a small diameter state between an inner shaft 24 and an outer shaft 25 which are axially shiftable relative to each other. The stent 23 is released by retraction of the outer shaft 25 so that the stent 23 can expand and conformingly support the inner wall of vessel portion 1. After the self-expanding stent 23 is fully set free the stent delivery instrument 22 is withdrawn through the insertion catheter 12 and can be removed completely from the first occlusion catheter 4.

According to FIG. 5, again a dilatation catheter 15' is introduced which may have different diametral and/or longitudinal sizes in its dilatation balloon 18'. It is used to perform a post-dilation if the treated stenosis has not yet reached the required patency and it further anchors the implanted stent 23 within the wall of the vessel portion 1.

Figure 6:
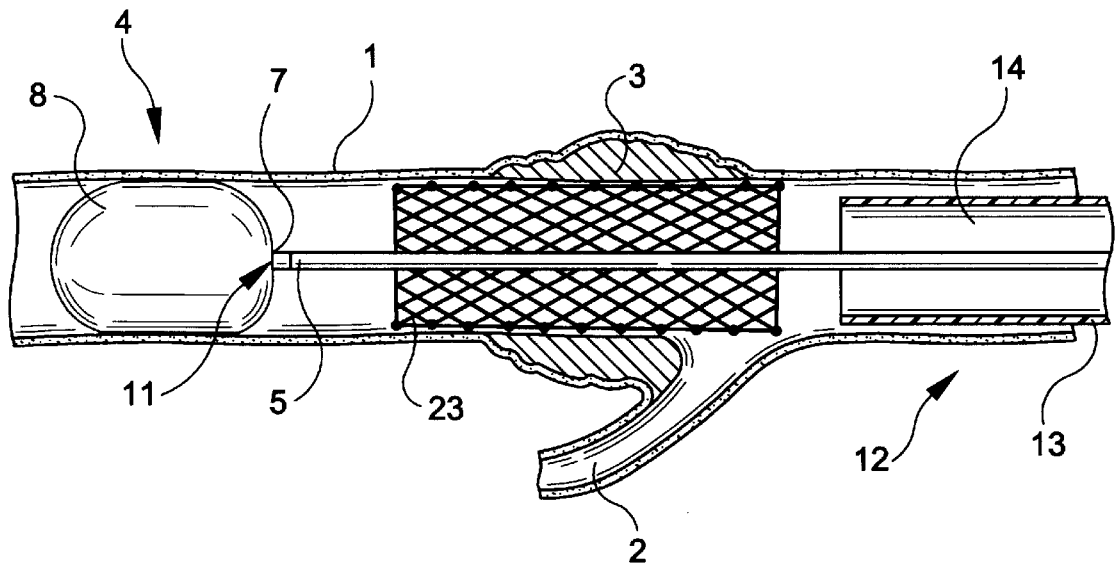

In FIG. 6 the dilatation catheter 15' is retracted and the stent 23 is engaged with the vessel portion 1 as desired. Before emptying the distal occlusion balloon 8 any particles which may have been detached from the vessel wall during the treatment are removed by suction via the through lumen 14 of the insertion catheter 12 as it is known from the state of the art.

The above-described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A catheter device for the treatment of a vessel carrying body fluid, comprising an inner occlusion catheter, having a first tubular shaft with a proximal end and a distal end, a distal occlusion balloon disposed at the distal end of the first tubular shaft and an inflation lumen extending through the first tubular shaft between a proximal entry at the proximal end and a distal exit inside the distal occlusion balloon, and an outer treatment catheter, having a second tubular shaft with a central lumen extending therethrough for coaxial reception of the first occlusion catheter, and being longitudinally displaceable with respect to the first occlusion catheter, the first tubular shaft inflation lumen having a proximal entry seal having an outside dimension small enough to fit within the central lumen for advancing and withdrawing the treatment catheter onto and from, the inner occlusion catheter.

2. The catheter device of claim 1 wherein the treatment catheter is a dilatation catheter further having a non-compliant dilatation balloon.

3. The catheter device of claim 2 wherein the dilatation catheter further comprises a balloon-expandable stent mounted on the dilatation balloon.

4. The catheter of claim 1 wherein the treatment catheter is a stent delivery instrument loaded with a self-expanding stent.

5. The catheter of claim 1 wherein the treatment catheter comprises a second occlusion catheter further having a proximal occlusion balloon for sealing a vessel portion between the proximal and distal occlusion balloon.

6. The catheter device of claim 5 having an annular lumen disposed between the first and second tubular shafts and extending between a proximal inlet and a distal outlet for the infusion and aspiration, of a liquid into and from, the sealed vessel portion.

7. The catheter device of claim 1 further comprising an outer insertion catheter having a third tubular shaft with a through lumen for insertion and retraction, of the occlusion catheter and of the treatment catheter into and from, the vessel.

8. A catheter system comprising:

a first catheter including a first tubular shaft having a proximal region, a distal region, and an inflation lumen with a proximal entry disposed in the proximal region;

an inflatable balloon having an interior and being disposed at the first tubular shaft distal region, the inflation lumen extending through the first tubular shaft between the proximal entry and the balloon interior and being in fluid communication with the proximal entry and the balloon interior;

a proximal entry seal for sealing the proximal entry; and a second catheter including a second tubular shaft having a proximal region, a distal region, and a lumen extending within the second tubular shaft between the proximal and distal regions, wherein the second tubular shaft lumen is sized to receive the first tubular shaft proximal region therein and the first tubular shaft proximal entry seal is sized to be slideably received within the second tubular shaft lumen.

9. A catheter system as recited in claim 8 wherein the second catheter includes a distal inflatable balloon.

10. A catheter system as recited in claim 8 wherein the second tubular shaft lumen includes an annular lumen defined by the second tubular shaft and the first tubular shaft disposed therein, and the annular lumen has a distal outlet for infusing fluid through the second tubular shaft lumen and through the annular lumen distal outlet.

11. A catheter system comprising:

a first balloon catheter including a first tubular shaft, a proximal region, a distal region, a distal inflatable balloon having an interior, an inflation lumen extending through the first tubular shaft between a proximal entry in the proximal region and the distal region and being in fluid communication with the balloon interior;

a second catheter having a second tubular shaft, a proximal region, a distal region, a lumen therethrough, the lumen sized to receive the first tubular shaft proximal region therein;

means for sealing the first catheter proximal entry; and means for proximally removing the second catheter over the first catheter while the first catheter is sealed.

* * * * *